United States Patent Office.

CHARLES L. LEGE, OF SAN ANTONIO, TEXAS.

*Letters Patent No.* 65,580, *dated June* 11, 1867; *reissue No.* 2,912, *dated April* 7, 1868.

IMPROVED MEDICINAL PREPARATION.

The Schedule referred to in these Letters Patent and making part of the same.

TO ALL WHOM IT MAY CONCERN:

Be it known that I, CHARLES L. LEGE, of San Antonio, Bexar county, Texas, have invented a new and improved Medical Compound; and I do hereby declare that the following is a full, clear, and exact description thereof, which will enable others skilled in the art to make and use the same.

This invention relates to a new medical preparation which is to be a substitute for the medicaments now generally used for poultices, and also for internal medicine.

My invention consists in the application of the dried and powdered leaves, stalks, and joints of the *Cactus opuntia* or *cochinilifer*, for poultices or other medical preparations.

It has been found that this powder is more mucilaginous, more cooling and effective than flax-seed, slippery elm, and other preparations generally used for poultices. It has no sour or bad smell, nor is it offensive when used, or subject to putrid or acid decomposition, and it remains moist and effective for a longer period than the other preparations used for poultices. But besides being used in the said preparation, my powder may also be used for other medical purposes, either alone or in combination with other matter. It may be applied internally as well as externally, and I do not wish to confine its use to any particular application or manner of application.

To make the powder, the leaves, stalks, or joints of the aforesaid cactus are or may be freed of their rind and spines, so that the most fleshy and pulpy portions may remain, which are then, either whole or cut and split, submitted to a suitable heating or drying process, by which they will be rendered perfectly dry and crisp. They are then ground or powdered into a powder of suitable fineness, which may, if desired, be bolted, so as to have various assorted sizes.

I do not confine myself to any particular mode of producing the powder from any portion of the aforesaid plant, nor to any particular treatment to which the said plant or the powder may be submitted before it is ready to be applied; but I do claim as new, and desire to secure by Letters Patent—

A medicament produced from the material specified.

Witnesses:

A. V. BRIESEN,

ALEX. F. ROBERTS.

CHAS. L. LEGE.